United States Patent
Knuebel et al.

(10) Patent No.: US 10,959,665 B2
(45) Date of Patent: Mar. 30, 2021

(54) DETERMINING THE THICKNESS OF HAIR ON THE HEAD IN A DAMAGE-FREE WAY

(71) Applicant: Henkel AG & Co. KGaA, Duesseldorf (DE)

(72) Inventors: Georg Knuebel, Duesseldorf (DE); Lucile Bonnin, Duesseldorf (DE); Andreas Kirch, Wuppertal (DE)

(73) Assignee: Henkel AG & Co. KGaA, Duesseldorf (DE)

(*) Notice: Subject to any disclaimer, the term of this patent is extended or adjusted under 35 U.S.C. 154(b) by 105 days.

(21) Appl. No.: 16/219,699

(22) Filed: Dec. 13, 2018

(65) Prior Publication Data

US 2019/0183409 A1 Jun. 20, 2019

(30) Foreign Application Priority Data

Dec. 14, 2017 (DE) ...................... 10 2017 222 747.8

(51) Int. Cl.
*G06K 9/00* (2006.01)
*A61B 5/00* (2006.01)
(Continued)

(52) U.S. Cl.
CPC ............ *A61B 5/448* (2013.01); *A61B 5/1072* (2013.01); *A61B 5/1079* (2013.01); *A45D 2044/007* (2013.01); *G16H 30/40* (2018.01)

(58) Field of Classification Search
CPC combination set(s) only.
See application file for complete search history.

(56) References Cited

U.S. PATENT DOCUMENTS

2001/0014180 A1* 8/2001 Ejiri .......................... G06T 5/50
  382/275
2002/0049432 A1* 4/2002 Mukai ................ A61B 18/203
  606/9
(Continued)

FOREIGN PATENT DOCUMENTS

JP  2006181100 A  7/2006
JP  2008241256 A  10/2008
(Continued)

OTHER PUBLICATIONS

Huffmann, A Novel Tool for the Analysis of Hair Growth, 2003 (Year: 2003).*

*Primary Examiner* — Alex Kok S Liew
(74) *Attorney, Agent, or Firm* — Lorenz & Kopf, LLP

(57) ABSTRACT

Devices and methods for determining the thickness of hair are provided. An exemplary device includes a computing unit with a processor and a local memory. The processor is connected to the local memory and configured to read data from and/or to write data into the local memory. The device further includes a user input/output unit configured for interaction with a user. Also, the computing unit includes an image data input interface for receiving image data of at least one individual hair. The image data input interface is connected to the processor. Further, the computing unit includes a user interface connected to the user input/output unit and to the processor. The computing unit is configured to process the image data of the at least one individual hair to create hair thickness values of the at least one individual hair and to output the hair thickness values to the user interface.

17 Claims, 3 Drawing Sheets

(51) Int. Cl.
  *A61B 5/107*  (2006.01)
  *G16H 30/40*  (2018.01)
  *A45D 44/00*  (2006.01)

(56) References Cited

U.S. PATENT DOCUMENTS

| | | | | |
|---|---|---|---|---|
| 2008/0063292 A1* | 3/2008 | Nose | ............ | G06T 5/006 382/243 |
| 2010/0054592 A1* | 3/2010 | Nanu | ............ | H04N 5/23219 382/167 |
| 2012/0320191 A1* | 12/2012 | Meschkat | ............ | A61B 5/448 348/135 |
| 2013/0308823 A1* | 11/2013 | Smith | ............ | G01N 33/4833 382/103 |

FOREIGN PATENT DOCUMENTS

| | | | |
|---|---|---|---|
| JP | 2010082245 A | 4/2010 | |
| WO | 2016193018 A1 | 12/2016 | |
| WO | 2017072009 A1 | 5/2017 | |

\* cited by examiner

DETERMINING THE THICKNESS OF HAIR ON THE HEAD IN A DAMAGE-FREE WAY

CROSS-REFERENCE TO RELATED APPLICATION

This application claims priority to German Patent Application No. 10 2017 222 747.8, filed Dec. 14, 2017, which is incorporated herein by reference in its entirety.

TECHNICAL FIELD

The present disclosure relates to a device for determining the thickness of hair, a method for determining the thickness of hair, and a computer program product which is designed to be executed on a computing unit.

BACKGROUND

In the case of some cosmetic and non-therapeutic treatments of human hair, in particular hair on the head, it can be relevant to know what the thickness is of the hair to be treated. In conjunction with this description, the thickness of hair is understood in particular to be a diameter of an individual hair if it is assumed that an individual hair has a round or circular cross-section, which is fundamentally the case.

To be able to determine the thickness of hair, a tuft of hair can be cut from a person and supplied for analysis. This makes it possible to determine the thickness of the individual hairs and to demonstrate a distribution of the values of the hair thickness over a value range using statistical methods. This approach, however, requires a certain amount of hair, i.e. a sample, to be taken and supplied for analysis. In some circumstances the analysis is performed at another location and, due to the transport of the hair sample and confirmation of the results, already requires a not insignificant period of time before the results of the analysis are provided and a decision can be made as to the further course of procedure for the treatment.

Accordingly, it is desirable to provide user-friendly and effective strategies in order to determine the thickness of hair which deliver the result within a short space of time and without invasive handling of the hair on a person's head.

BRIEF SUMMARY

Devices and methods for determining the thickness of hair are provided. An exemplary device for determining the thickness of hair includes a computing unit with a processor and a local memory. The processor is connected to the local memory and configured to read data from the local memory and/or to write data into the local memory. The device further includes a user input/output unit configured for interaction with a user. Also, the computing unit includes an image data input interface for receiving image data of at least one individual hair, wherein the image data input interface is connected to the processor. Further, the computing unit includes a user interface connected to the user input/output unit and to the processor. The computing unit is configured to process the image data of the at least one individual hair to create hair thickness values of the at least one individual hair and to output the hair thickness values to the user interface.

In another embodiment, a method for determining the thickness of hair using a computing unit is presented. The method includes reading out a captured image of a hair ensemble and supplying the captured image to the computing unit. Further, the method includes converting the captured image into a binary image. Also, the method includes determining hair thickness values in the binary image. The method further includes creating a chart regarding the hair thickness values and outputting the chart to a user surface.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

The object of the present disclosure can be considered to be that of specifying a device and an associated method which make it possible to determine the thickness of hair within a short space of time, more specifically without damaging the hair or having to at least partially cut the hair.

This object is achieved by the features of the independent claims. Developments of the present disclosure will emerge from the dependent claims and from the following description.

In accordance with one aspect, a device for determining the thickness of hair is specified. The device includes a computing unit and a user surface. The computing unit includes a processor and a local memory, wherein the processor is connected to the local memory such that the processor can read data from the local memory and/or can write data into the local memory. The user surface is used as an input unit and/or output unit for interaction with a user. The computing unit also includes an image data input interface for receiving image data of a hair ensemble including of at least one individual hair, wherein the image data input interface is connected to the processor, and a user interface which is connected to the user surface and to the processor. The computing unit is designed to process the image data of the hair ensemble and in so doing to create a bar chart regarding the hair thickness values occurring in the hair ensemble and to output the bar chart to the user interface.

The device described here makes it possible to measure the hair, in particular human hair on the head, in a destruction-free way. This means that the hair does not have to be trimmed in order to determine the hair thickness. The device and the method carried out therewith are for example suitable for proving the efficacy of methods for thickening hair or for mechanical tests. Hair thickening can be carried out for example using a swelling method which can expand the hair cross-section, or using coatings, for example polymer coatings. Mechanistic tests can be used for example in coloring processes and in particular in the case of permanent waving so as to observe occurring swelling and shrinking processes of hair. With the aid of the described device and the associated method, it can be made possible to observe swelling and shrinking processes of this kind non-invasively as they occur and without a significant time delay. It is possible to draw conclusions as to the efficacy of products on the basis of such observations. These conclusions can be collected in the device and evaluated for product modification and product adaptation.

The knowledge of the hair thickness of the hair on a person's head can be of significance for various measures on the hair on the head. These measures can be in particular cosmetic and non-therapeutic in nature. For example, the treatment agents to be applied so as not to damage the hair may be dependent on the thickness of the hair. The device described here makes it possible to determine the thickness of the hair in a simple way.

The processor can contain a logic circuit which can perform a large number of functions and can be configured as required to perform a series of commands. This series of commands is typically referred to as a program or software. The processor can be a hard-wired logic circuit or a programmable logic circuit, for example a programmable processor, such as a microprocessor or an FPGA (field programmable gate array) module. The processor can be any kind of computer program, for example a computer program in programming code for a virtual machine (separate runtime environment, virtual machine), for example a Java computer program.

The local memory can be a volatile or permanent memory, and in particular a rewritable and/or readable memory. The image data can be stored in the local memory and can be read for processing. The processed image data can be stored in modified form in the local memory, for example for further processing steps.

The user surface is an arrangement for interacting with a human user including at least one input unit (keypad, mouse, microphone, touchscreen) and/or at least one output unit (display unit, display, loudspeaker). For example, the user surface may be a touch-sensitive display and the human user can interact directly with the displayed content by touching a certain area of the display.

Image data can be read via the image data input interface, for example can be read from an image data memory or directly from an image-capturing unit. It is conceivable that an image data memory having a large amount of image data (individual images of hair ensembles from one or more people) is provided and is connected to the image data input interface. The image data is then read in and a bar chart regarding the values of the hair thickness is created for each individual image. It is furthermore conceivable that the computing unit reads out meta information (identification data of an image in order to identify the imaged person, data of capture, etc.) from the individual images and displays at least some of this meta information in the associated bar chart. It is possible via the meta information to assign a number of individual images to the same person and to combine the values from these images in a single bar chart. For example, a number of images of different regions of the hair on a person's head can be provided and it may be desirable to display the information from all of these images in a single bar chart in order to provide an overview of the entire state of the hair on the head of the person in question.

A hair ensemble in the context of this description is understood to mean a captured image of one or more individual hairs. The position and orientation of the hair is not necessarily relevant. For example, the hair can be captured against a yellow background or generally against a background with a color which contrasts with the color of the hair. Blonde hair can be captured in front of a dark background, and by contrast dark hair can be captured against a light background. To this end, the hair can be arranged on a flat element and can bear against the surface of this flat element. The individual hairs are thus preferably distributed over this surface, such that individual hairs can be identified in the image data.

It is conceivable that the hairs bearing against the surface are pressed by employing a transparent flat element against the surface in order to ensure that the distance of the individual hairs from an optical group of an image-capturing unit which generates the image data is uniform. Distortions in the captured image can hereby be reduced or avoided, which ultimately increases the accuracy of the determined hair thickness values.

The hair thickness can be specified in pixels or in any length unit (for example in metric units), provided the scale of the captured image is known. The scale of the captured image can be an allocation of a pixel to the desired length unit. Here, the hair thickness corresponds to the diameter of an individual hair, i.e. the extent of a hair transversely to the longitudinal direction in a two-dimensional captured image of a hair ensemble.

Individual human head hairs or hairs on the head generally have a diameter of from about 50 to about 100 µm. The captured image of the hair ensemble can have a scale or resolution for example of about 5 µm per pixel. In the above-stated value range for the diameter, this resolution corresponds to an accuracy of from about 5% to about 10% based on the hair diameter.

The user interface emits signals to the user surface and the user surface converts these signals into information that can be assessed by a human user, for example into audio signals or video signals, in particular static image signals. The user interface also receives inputs of a human user and forwards these inputs to the processor.

The user surface can display for example the image data forming the basis of the analysis and at the same time or subsequently the bar chart of the hair thickness values.

The bar chart regarding the hair thickness values occurring in the hair ensemble indicates which values occur and how often. The frequency can be a relative frequency which is based on the total number of all determined hair thickness values.

In other words, the device described here makes it possible to use image-analytical methods to determine the thickness of hair. The device requires, as input data, merely an image of the hair on a person's head in sufficient magnification or resolution. An image of this kind can be created for example using a digital microscope.

For example, the diameter J method (https://imagej.net/DiameterJ) can be used as image-analytical method.

In accordance with one embodiment the computing unit is designed to receive a greyscale image via the image data input interface and to convert the greyscale image into a binary image before the bar chart regarding the hair thickness values occurring in the hair ensemble is created.

A binary image assumes for each pixel precisely one state of a total of two possible states. For example, each pixel can be either white or black. This has the advantage that the state of the individual pixels can be easily identified and the pixels can be clearly distinguished from one another.

In accordance with a further embodiment the computing unit is designed to specify the hair thickness values in the bar chart in pixels.

A number of thickness values can be determined for one individual hair. It is for example conceivable that an individual hair is divided into a number of length portions and the thickness is determined and shown for each length portion. Although it is assumed that an individual hair has substantially the same thickness over its length (the hair tip or an end portion of a hair might have a smaller thickness than the other length portions), this approach can thus increase the number of measured values in order to reduce the influence of measurement errors or image errors.

If the diameter of an individual hair is specified in pixels, this specification relates to the number of image points between a first edge of the hair and the opposite edge of the hair. For this purpose, the computing unit may plot a vertical line starting from a point of the edge of the hair and determine the number of pixels which are passed through by this vertical line before the vertical line reaches the opposite edge.

In order to increase the measurement accuracy, in this approach hairs or length portions of hairs running at an incline can be excluded from the consideration because in this case it may be that the vertical line, on account of its likewise inclined course, intersects a significantly increased number of pixels before the vertical line reaches the opposite edge. This consideration is true for a matrix-like structure of the images with horizontally running rows and vertically running columns of pixels.

In the bar chart the number of the associated measurements is plotted for each measured hair thickness value (for example on a scale with about 5 µm increments, i.e. about 50 µm, about 55 µm, about 60 µm . . . about 100 µm). This then gives the relative the frequency of each hair thickness.

In accordance with a further embodiment the computing unit is designed to determine a scale of the hair ensemble in a predefinable length unit and to convert the hair thickness values into the predefinable length unit and to show these in the bar chart.

The scale can be determined for example by inserting an element (can also be referred to as reference element) with known dimensions (length and/or width) into the hair ensemble before the image of the hair ensemble is captured. The element can be bar-shaped, for example.

The hair ensemble can be placed for example for the image capture on a flat element having a light surface. A dark bar of known width can be imaged on this surface. This bar can be used as a reference element.

In order to identify the reference element, it can be marked via the user interface by a user in the captured image of the hair ensemble. Alternatively or additionally, the reference element can have an optically identifiable and evaluable pattern so as to be recognized automatically by the computing unit. This pattern for example could be formed from a multiplicity of light regions at regular distances along a longitudinal direction of the reference element. The light regions can additionally have the same shape in order to facilitate an automated recognition of the reference element. The light regions can have an asymmetrical form so as to be able to recognize a position or orientation of the reference element. The reference element can comprise length portions of different width. It is also conceivable that the width of the reference element can be derived from the distance between the light regions along the reference element. For example, the distance between the light regions can thus be an integer multiple of the width of the reference element.

It should be noted that the light regions of the reference element are cited above by way of example that the width of the reference element can be derived in principle from a light-dark pattern of the reference element.

With the aid of the reference element it can also be determined whether the captured image of the hair ensemble is optically distorted. A distortion of this kind can then also be compensated for by employing the known dimensions of the reference element.

It is conceivable that two reference elements can be used for the capturing of an image of a hair ensemble, one of which reference elements runs horizontally and the other of which runs vertically, so as to be able to detect and also compensate for distortions in both directions.

In accordance with a further embodiment the computing unit is designed to output the image data of the hair ensemble on the user surface, wherein the user surface is designed to receive an input which denotes a region of the hair ensemble and to transmit this input to the computing unit, wherein the computing unit is also designed to limit the bar chart regarding the hair thickness values occurring in the hair ensemble to the region denoted in the input.

It is thus possible to supply different regions of the hair ensemble to an analysis of hair thickness. For example, the captured image of the hair ensemble can cover a certain length portion of individual hair or even the entire length of the individual hair. In this embodiment it is possible to analyze various regions of the captured image separately from one another. For example, the ends of the hair can be analyzed separately from a middle portion and also separately from a portion of the hair close to the scalp.

It is of course also conceivable that various captured images of various regions of the hair are created and supplied for evaluation in order to gain information regarding the thickness of the hair in various regions.

In accordance with a further embodiment the computing unit is designed to determine treatment agents and/or use instructions for treatment agents for the hair on the basis of the bar chart of hair thickness and to output these agents and/or instructions to the user surface.

On the basis of the determined hair thickness, treatment agents and/or use instructions of these treatment agents or general use instructions of treatment agents for the hair can be determined and output to a user with the aid of the user surface, for example displayed or presented. Some treatment means might be less advisable for certain hair thickness values. The use of the treatment agents may also be dependent on the hair thickness values.

If the hair thickness drops below a certain value, it can be advantageous that treatment agents and/or use instructions for increasing hair thickness are output to the user. Treatment agents for increasing the hair thickness can advantageously comprise ingredients selected from the group including of xanthine compounds, vitamin B3 compounds, panthenol compounds or a mixture thereof. The xanthine compound is advantageously selected from caffeine xanthine, 1-methyl-xanthine, theophylline, theobromine and mixtures thereof. The vitamin B3 compound formed from niacinamide and salts thereof, niacin and salts thereof, nicotinyl alcohol and salts thereof, nicotinic acid esters, nicotinyl amino acids, nicotinyl esters of carboxylic acids, nicotinic acid-N-oxide, niacinamide-N-oxide, and mixtures thereof. The panthenol compound is advantageously selected from D-panthenol, DL-panthenol, panthenyl triacetate, panthetine, panthotheine, panthenyl ether ether, and mixtures thereof.

It is conceivable that a query catalogue is presented to the user via the user surface so as to query further relevant information from the user in addition to the optically detected information regarding the hair. This further information can relate to previous haircare and hair treatment, but also to the age, gender, ethnicity and lifestyle and dietary habits. This further information can likewise be included in the determination of a suitable treatment agent and/or use instructions, in addition to the bar chart regarding the hair thickness.

The device described here makes it possible to easily determine certain treatment agents and/or use instructions for the hair of a person and to display these agents and/or instructions to a user.

Information regarding the treatment agents and/or use instructions can be stored in the local memory and can be determined by the computing unit depending on the hair thickness or the bar chart regarding the hair thickness of a person. To this end, the information regarding the hair thickness is used by the processor in order to read from the local memory those treatment agents and/or use instructions associated with the determined hair thickness or suitable for same.

It is of course also possible that the information regarding the treatment agents and/or use instruction for same are made available at least in part in a remote memory. This remote memory can be part of a server or a group of servers which can be reached via a public or private communication network. This server or this group of servers can also be referred to as an external computing unit and will be described further below.

In one exemplary embodiment the user interface is designed, after the output of features of a treatment agent, to receive an input from a user and on the basis of this input to prompt an action relating to the output treatment agent.

The action for example can relate to the fact that a treatment agent is offered for sale to the user, and the user can arrange to make this purchase via an input. Besides the purchase of treatment agents, the user can also be provided with further information for the purchase. This further information can relate to more detailed treatment and use instructions. The user interface for example receives the input that the user wishes to purchase the treatment agent, stores the query and/or transmits the query to a retailer who sells the treatment agent. The user is requested by the computer program to input his personal data (address, bank information, shipping preference, etc.) via the input unit. Alternatively, it can be output to the user where he can purchase the output treatment agent locally, in his vicinity, for example at a chemist's, a pharmacy, etc.

In accordance with a further embodiment the computing unit and the user surface are arranged in a common housing.

The computing unit and the user surface can be part of a computer, for example. The computer can be a portable user device, for example a smartphone, phablet, or a tablet computer or a laptop.

In accordance with a further embodiment the computing unit includes a data transmission interface, wherein the data transmission interface is designed to exchange data with an external computing unit via a transmission path or generally a data network.

This can serve for the computing unit to transmit image data of the hair ensemble fully or partially to the external computing unit so that the image data is analyzed by the external computing unit. This can be advantageous if the analysis of the image data requires high computing power which the (local) computing unit cannot provide.

For example, the image data of the hair ensemble can be transmitted directly after receipt by the (local) computing unit to the external computing unit. It is also conceivable, however, that merely the image data relevant for an analysis is transmitted to the external computing unit, for example once a user has selected or determined a region of the image data on the user surface for the analysis.

The external computing unit can be arranged spatially separately from the device for determining the thickness of hair (also: local computing unit). The local computing unit can be connected to the external computing unit, i.e. can be connected thereto for communication therewith, via the data network. The external computing unit can be an individual computer or processor or a composite of computers or processors. The computing load can be divided in a computer or processor composite among the individual constituents of the composite from various viewpoints.

This computing composite, besides computing power, can also provide storage capacities for the user and can provide data released or indicated by the users. The memory space required in the local computing unit can thus be reduced. It is also made easier for the user to replace a local computing unit because no or almost no data is stored locally. The computing composite can be embodied as a group of servers crosslinked in an intermeshed manner.

In accordance with a further embodiment the device as described herein also includes am image-capturing unit. The image-capturing unit is designed to create a captured image of a hair ensemble. The image-capturing unit is also coupled to the image data input interface in order to transmit the captured image of the hair ensemble to the processor, The image data input interface can enable wireless or wired communication between the computing unit and the image-capturing unit. For example, the image-capturing unit can be coupled to the computing unit via what is known as a USB interface (universal serial bus) or via a wireless communication protocol from the group of IEEE 802.11 (WiFi, wireless LAN) or IEEE 802.15 (wireless personal area network, close-range networks).

In a further example, for the connection of the image-capturing unit to the computing unit, protocols can also be used that work in accordance with the principles of mesh networks. For example, the thread protocol, which is based on IPv6, can be used for the data transmission and for the connection of the image-capturing unit to the computing unit. The thread protocol is used in particular to connect automated or partially automated devices to one another.

The image-capturing unit can be structurally fitted onto the computing unit in one example, or conversely the computing unit can be fitted onto the image-capturing unit or connected thereto. This means that the image-capturing unit is mechanically fastened to the computing unit or a housing of the computing unit, or vice versa. For example, this can be achieved by tool-free assembly via a reversible connection. In the fitted position, the image-capturing unit can be held relative to the computing unit by employing a releasable frictionally engaged or form-fitting connection. The interfaces between image-capturing unit and computing unit can be arranged such that in the fitted position an electrical connection is produced or established automatically between the image-capturing unit and the computing unit. Alternatively, the computing unit and image-capturing unit can be structurally separated from one another, wherein a data connection as described above is established between the two. The image-capturing unit can comprise for example a microscope attachment for smartphones, for example the Scrona µPeek.

The computing unit can run an application (or a program) which receives or queries data from the image-capturing unit. The received or queried data is assessed in the application so as to determine one or more output values, i.e. to display image data of a hair ensemble and/or to determine and to display an associated bar chart. The data is processed and/or evaluated by the application in accordance with the approaches described herein.

In order to run the application, processors (and one or more memory modules) of the computing unit can be used. The computing unit, however, can also be configured to outsource computing steps for the running of the application. The application for example can thus transmit the data obtained or queried from the image-capturing unit to an external computing unit. Before the data is transmitted to the external computing unit, it can be supplied to a pre-processing.

In accordance with a further embodiment the device also includes a reference face, wherein the reference face is coupled via a holding element to the image-capturing unit, and wherein the reference face is configured for placement of a hair ensemble.

The reference face is preferably movable relative the image-capturing unit so as to be able to adjust the distance between the reference face and the image-capturing unit. To this end, the holding element may comprise a joint or another adjustment element.

The reference face constitutes the reference face already described above. A reference element can be imaged on the reference face so as to determine a scale in the captured image. It is conceivable that a vertical bar and/or a horizontal bar of predefined width and/or length is imaged on the reference face. If a captured image of a hair ensemble is created, it may be expedient if the reference elements are not covered by hairs.

In accordance with a further aspect the use of a device described herein for determining the thickness of hair is specified.

In accordance with a further aspect a method for determining the thickness of hair including a computing unit is specified. The method includes the following step: reading out a captured image of a hair ensemble; supplying the captured image to the computing unit; converting the captured image into a binary image; determining values of the hair thickness in the binary image; creating a bar chart regarding the values of the hair thickness; outputting the bar chart to a user surface.

The method corresponds substantially to the functions of the device described herein. The explanations provided above and hereinafter in respect of the device apply similarly to the method.

In accordance with a further embodiment the method also includes the following step: transmitting the captured image to an external computing unit, wherein the steps of converting the captured image into a binary image and of determining values of the hair thickness in the binary image are performed at least partially by the external computing unit and the results of these steps are transmitted back to the computing unit.

In accordance with a further embodiment the method also includes the following step: determining a treatment agent and/or use instructions for treatment agents on the basis of the bar chart regarding the hair thickness values, and outputting the treatment agent and/or the use instructions.

In accordance with a further embodiment, the hair thickness values in the binary image are determined in pixels and/or in a predefinable length unit.

In accordance with a further aspect a computer program product is specified which is configured to instruct a processor of a computing unit to perform the steps of the method described herein when the computer program product is executed on the processor.

BRIEF DESCRIPTION OF THE DRAWINGS

Exemplary embodiments of the present disclosure are shown in the drawings and will be explained in greater detail hereinafter. In the drawings.

DETAILED DESCRIPTION

Reference is made in the following detailed description to the accompanying drawings which form part of the present application and in which specific embodiments in which the present disclosure can be implemented are shown by way of illustration. It goes without saying that other embodiments can be used and structural or functional or logical modifications can be made without departing from the scope of protection of the present disclosure. In this regard, direction-related terminology such as "above", "below", "in front of", "behind", "front", "rear", etc. is used in respect of the orientation of the described figure(s). Since components of embodiments can be positioned in a number of different orientations, the direction-related terminology is used for illustration and is in no way limiting. It goes without saying that the features of the various exemplary embodiments described herein can be combined with one another unless explicitly stated otherwise. The following detailed description therefore should not be interpreted in a limiting sense, and the scope of protection of the present disclosure is defined by the accompanying claims and equivalents thereof.

Figure 1:
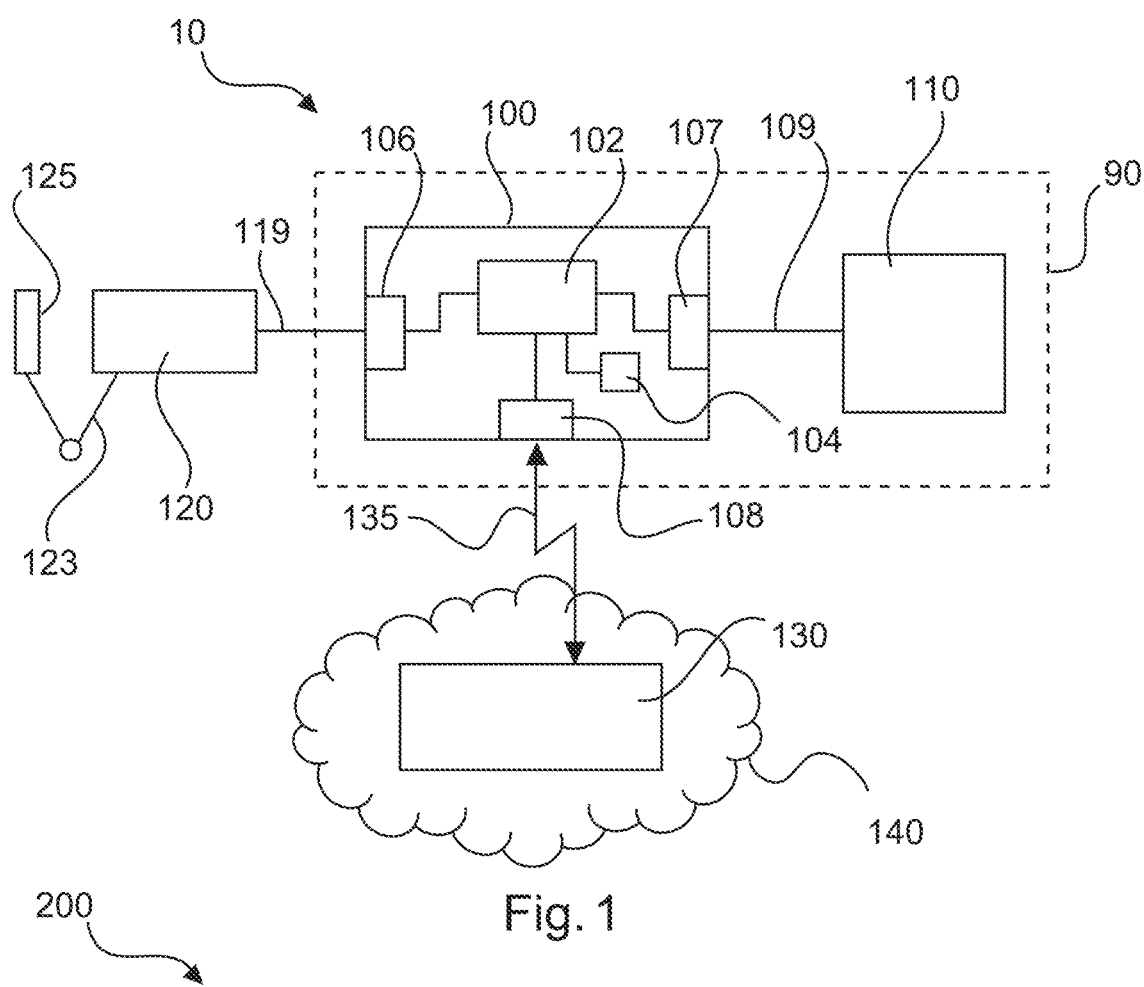
FIG. 1 shows a schematic illustration of a device for determining the thickness of hair in accordance with one exemplary embodiment.

FIG. 1 shows a device 10 for determining hair thickness. The device 10 includes a computing unit 101 and a user surface 110. The computing unit 100 and the user surface 110 can be arranged in a common housing 90. The device 10 can optionally comprise an image-capturing unit 120 and a reference face 125 which is coupled by employing a holding element 123 to the image-capturing unit 120.

The computing unit 100 is configured to determine the hair thickness of imaged hair from image data of a hair ensemble. The image data is provided by the image-capturing unit 120. Alternatively, the image data can also be read from an image data memory.

The holding element 123 can be configured to modify the distance between the image-capturing unit 120 and the reference face 125, such that a hair ensemble bearing against the reference face 125 can be optically detected.

The computing unit 100 includes: a processor 102, a local memory 104, an image data input interface 106, a user interface 107, and a data transmission interface 108. The image data input interface 106 is used to produce a connection between the computing unit 100 and the image-capturing unit 120, such that image data can be transmitted from the image-capturing unit 120 to the computing unit 100. In particular, the image data is transmitted to the processor 102 and the processor 102 is configured to perform image-analytical methods in order to extract the requested information from the image data.

The processor 102 can access the local memory 104 in order to store the results of the image-analytical methods and/or to read out information from the local memory.

The processor 102 can output the image data via the user interface 107 to the user surface 110 and can visually present the device 10 to a human user. The user surface 110 includes output units and input units in order to enable interaction with the user. The user can make a selection in presented image data or can perform other inputs in order to control or influence image-analytical methods performed by the processor 102.

The processor 102 can be connected via the data transmission interface 108 and a corresponding transmission path 135 to an external computing unit 130. The external computing unit 130 can be part of a network 140 or can be reachable via the network 140. The network 140 may be a private or public wide area data network. The transmission path 135 can be used to exchange data between the computing unit 100 and the external computing unit 130. For example, it is possible to allow the mentioned image-analytical methods to be performed at least partially by the external computing unit 130 and to transmit the results to the computing unit 100.

The data connections 109, 119, 135 proceeding from the computing unit 100 to the user surface 110, the image-capturing unit 120 and the external computing unit 130 can be wireless or wires or can be configured as a combination of wireless or wired portions.

The data connections 109, 119, 135 can enable unidirectional or bidirectional data transmission between the connected units. The image-capturing unit 120 thus delivers image data relating to the captured hair ensemble to the computing unit 100, whereas the computing unit 100 can deliver control commands to the image-capturing unit 120, wherein the control commands specify how the image-capturing unit 120 works. In the case of a unidirectional data connection 119, which merely enables a data transmission from the image-capturing unit 120 to the computing unit 100, control parameters regarding input elements (buttons, switches, control dials, etc., not shown) can be specified at the image-capturing unit 120. The image-capturing unit 120 optionally includes display elements (not shown) which indicate a status of the image-capturing unit or the set control parameters. Alternatively, the image-capturing unit 120 can transmit the set control parameters also to the computing unit 100, where these parameters can be displayed optionally.

The computing unit 100 includes a processor 102 and a local memory 104. The computing unit 100 receives signals regarding features of the tested hair ensemble and on the basis of these features determines a recommendation regarding a non-therapeutic treatment of the hair ensemble. The non-therapeutic treatment can include recommendations for treatment agents and/or treatment instructions or use instructions for the particular surface region tested. Treatment instructions and use instructions are used synonymously in the context of this description and relate to instructions for the non-therapeutic treatment of the hair ensemble shown in the image data with use of selected treatment agents or also without a use of treatment agents. Treatment instructions can contain in particular the use of treatment agents or also measures to be taken or refrained from by the user. The treatment instructions for example may thus contain an indication of desired or undesired behavior following the use of a treatment agent. In order to determine a non-therapeutic treatment to be recommended, the captured features of the tested hair ensemble can be compared with fields of application, effects and use instructions of treatment agents and/or treatment instructions. Information regarding the treatment agents and/or treatment instructions can be stored in the local memory 104.

The local memory 104 can exist outside of and spatially separately from the computing unit 100. The computing unit 100 can access the local memory 104 via a data connection and can retrieve information regarding the treatment agents and/or treatment instructions stored there. This retrieved information is compared by the computing unit 100 with the captured features of the examined hair ensemble so as to determine appropriate recommendations for the non-therapeutic treatment of the tested hair ensemble. In other words, this means that the local memory 104 is queried with use of the determined features of the hair ensemble. Firstly, a large amount of stored information can be retrieved from the local memory in order to then filter this with use of the determined features of the hair ensemble and optionally treatment goals which are relevant for the treatment agents and/or treatment instructions. To this end, the data from the local memory is loaded into a volatile memory of the computing unit 100. Alternatively, however, the determined features of the hair ensemble can be consulted already when the information is retrieved from the local memory in order to retrieve only the relevant information from the local memory. For the purposes of this description, these two variants can be understood to have equivalent effects. The term "features of the hair ensemble" is understood in particular to mean the bar chart regarding the hair thickness values.

The user surface 110 can comprise an input unit and an output unit (not shown). The input unit makes it possible for the user to specify parameters for the operating principle and configuration of the computing unit 100, the image-capturing unit 120 and/or the user surface 110. The input unit can record information via various interfaces: a keypad, a mouse, a touch-sensitive display or a microphone (what is known as voice control). It is conceivable that any interface is used via which a human user can communicate with a computing unit and input or transfer data. The output unit can be a display or another display unit which outputs visual information to a user. The output unit can also have a loudspeaker via which acoustic information can be output. Visual information can be output on a touch-sensitive output unit, such that the output unit can also be used for a user to make inputs.

In one example the computing unit 100 is designed to query information from a user and to additionally consider this information when querying the local memory 104 so as to obtain features of treatment agents for the non-therapeutic treatment of the hair ensemble from the local memory 104 in accordance with the queried information.

The queried information can be captured by employing a predefined query catalogue, wherein a statement by the user is given more or less weight or is also selected from one of several possible responses. The predefined query catalogue can concern in particular the age, gender, ethnicity and lifestyle habits and unusual stresses on the part of the user, for example dietary habits, amount and quality of sleep, hydration, type of beverages drunk, use of stimulants (for example, nicotine, alcohol), professional activities, and leisure activities (how much time outside buildings in all weather, periods of residence in the mountains, visits to tanning salons). The queried information can also relate to a desired property or a property to be achieved of the hair ensemble or hair of the user.

Figure 2:
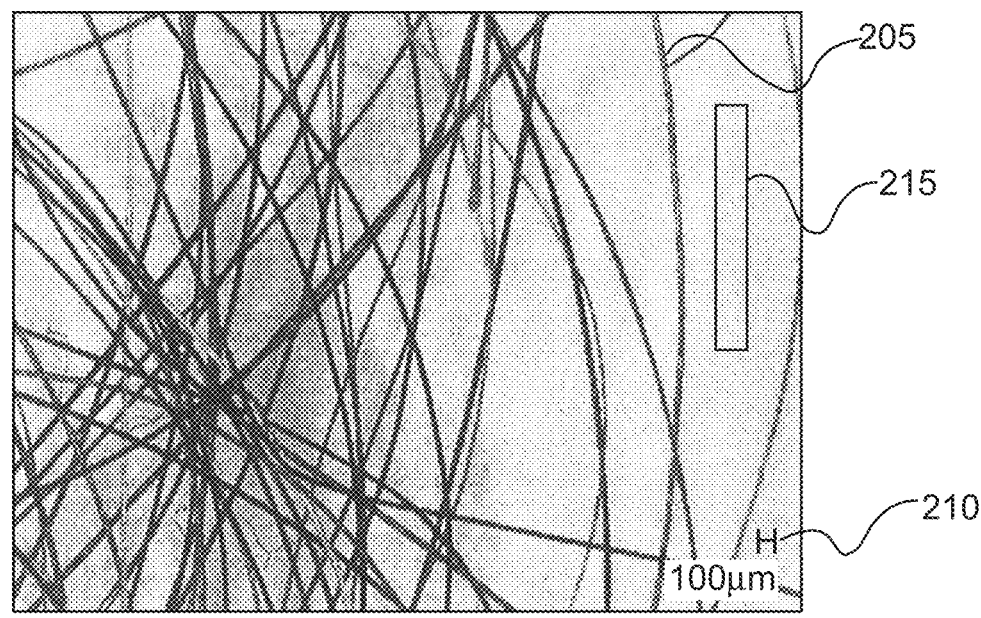
FIG. 2 shows a greyscale image of a hair ensemble.

FIG. 2 shows a highly enlarged greyscale image 200 of a hair ensemble of the hair on the head of a person. Multiple individual hairs 205 are shown herein. The scale 210 of this captured image is likewise shown. The thickness of the individual hair can be determined on the basis of this captured image. It is conceivable that a number of values for the thickness are determined for an individual hair, wherein these values relate to different length portions of the individual hair.

Besides the individual hairs 205, a reference element 215 is shown. The reference element 215 has known dimensions, such that the scale of the image can be determined on this basis. The use of the reference element 215 is optional. The scale can also be determined differently.

Figure 3:
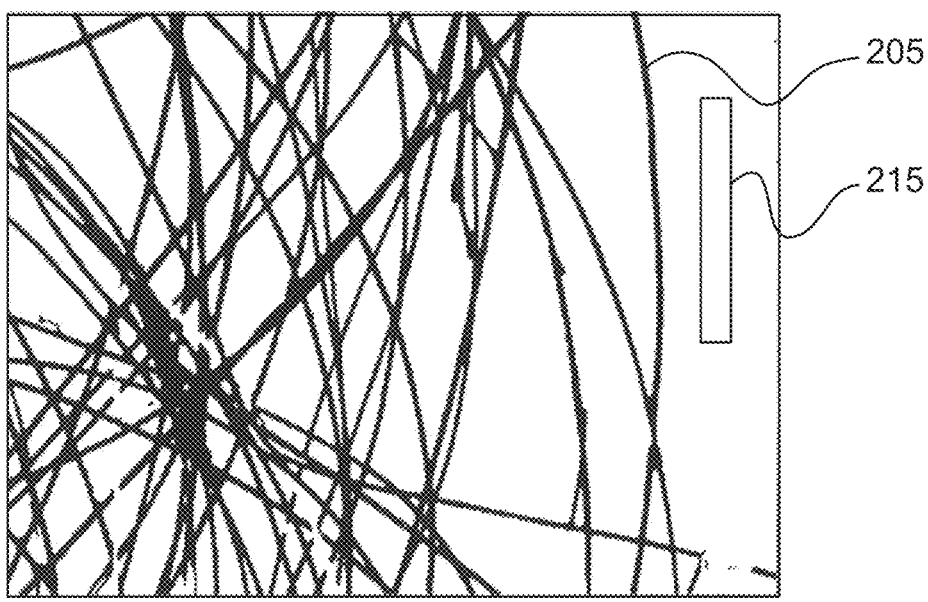
FIG. 3 shows a binary image of the greyscale image from FIG. 2.

A binary image is generated on the basis of the greyscale image of FIG. 2, in which binary image each individual image is assigned one of a total of two possible states. A binary image of this kind is shown in FIG. 3.

The binary image of multiple pixels (shown and explained in detail with reference to FIG. 7). The thickness of a hair at a certain point can be determined from the value of the individual pixels and the number of adjacent pixels of the same value. To this end, it may be necessary to apply more comprehensive image-analytical approaches in order to determine a length direction of a hair and to determine the thickness transversely or perpendicularly to the length direction of the hair.

Figure 4:
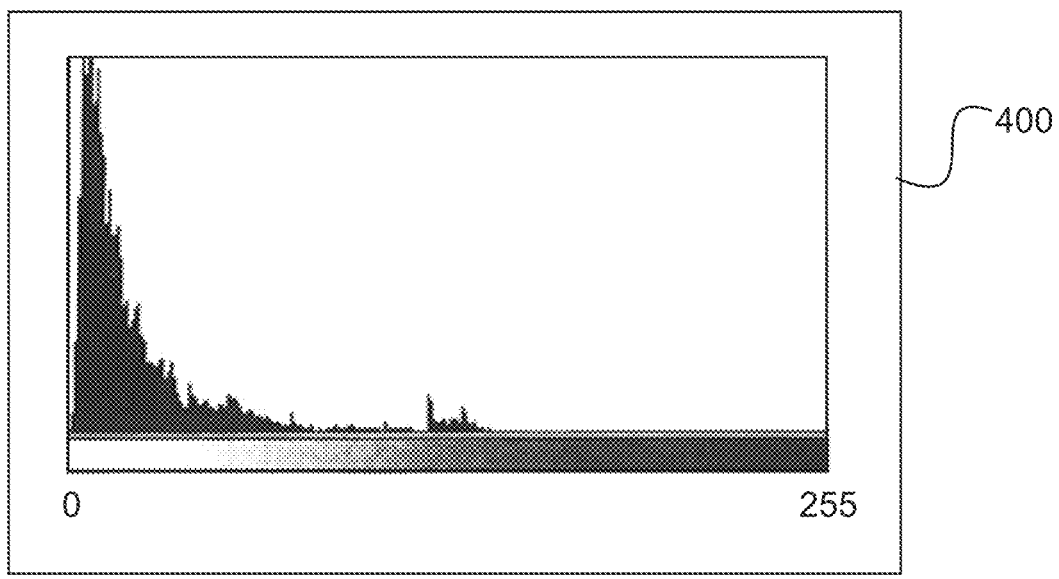
FIG. 4 shows an example of a bar chart of the hair thickness.

FIG. 4 shows a bar chart 400. In this bar chart the frequency or occurrence of a certain hair thickness value is shown. In the example of FIG. 4 the number of pixels is used as hair thickness value. If the resolution of the captured image (pixel/length unit) is known, the thickness can be concluded on the basis of the number of pixels.

For example, the resolution of a captured image of this kind can be 5 µm per pixel. The bar chart of FIG. 4 reveals a dense cluster of hair thickness values in the lower fifth of the value scale between 0 and 255 pixels and a significant reduction of the occurrence of the values to a little over half of the value scale.

Figure 5:
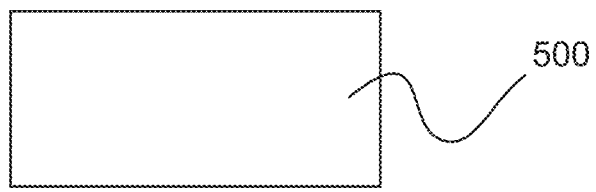
FIG. 5 shows a schematic illustration of a computer program product in accordance with one exemplary embodiment.

FIG. 5 shows a computer program product 500. The computer program product 500 is designed to instruct the processor 102 of the computing unit 100 to perform the functions or method steps described herein.

Figure 6:
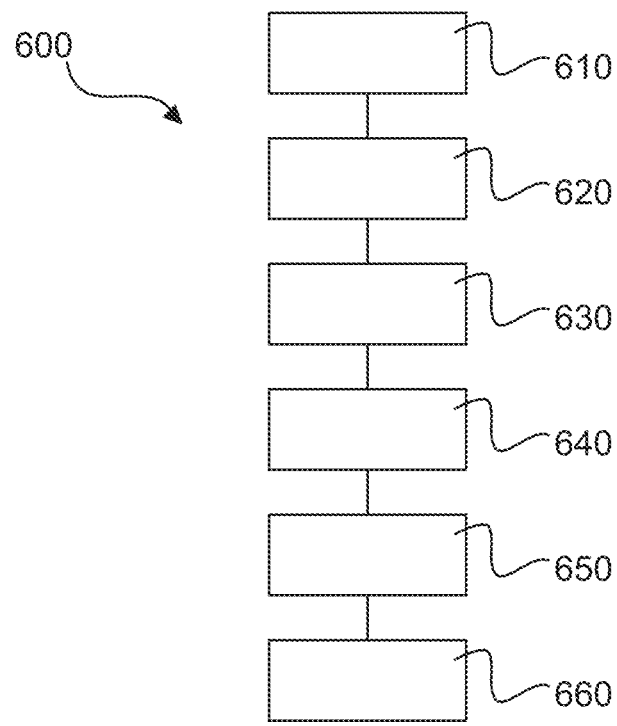
FIG. 6 shows a schematic illustration of a method in accordance with a further exemplary embodiment.

FIG. 6 shows a schematic illustration of a method 600 for determining the thickness of hair using a computing unit. The method includes the following step: reading out (610) a captured image of a hair ensemble; supplying (620) the captured image to the computing unit; converting (630) the captured image into a binary image; determining (640) values of the hair thickness in the binary image; creating (650) a bar chart regarding the values of the hair thickness; and outputting (660) the bar chart to a user surface.

The method 600 and steps thereof correspond substantially to the functions described in respect of the device 10. Reference is made at this juncture to the description of the device.

The method can also comprise further steps which are similar to the functions of the device 10.

Figure 7:
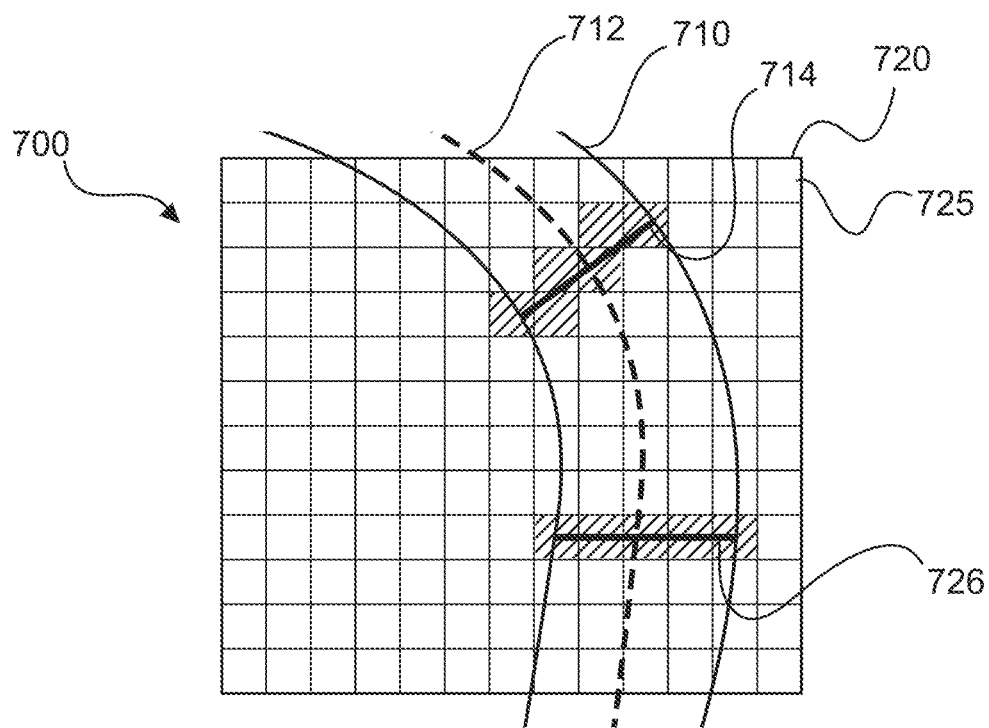
FIG. 7 shows an exemplary captured image of a hair in a pixel field of a device in accordance with one exemplary embodiment.

FIG. 7 shows a schematic illustration of an image 700 with a hair 710 shown significantly enlarged. The image 700 of a pixel field 720 with individual pixels 725. The pixels 725 are of the same size and are arranged in rows and columns.

The hair 710 runs firstly from top left to bottom right, then kinks such that it runs almost vertically downward from approximately half-height of the pixel field 720. A middle axis 712 of the hair 710 is shown by a dashed line.

In order to determine the thickness of the hair 710, the number of pixels that lie between the left edge and the right edge of the hair 710 can be determined. For example, a line can be plotted in the image at various positions, wherein this line intersects the middle axis 712 perpendicularly. The number of pixels through which the line runs from the left edge to the right edge can now be determined. This is done for example at two positions in FIG. 7, and the lines 714 and 726 are shown, and also the pixels passed through by these lines are marked by hatching.

The line 714 intersects six pixels and runs at an incline to the rows of the pixel field 720. The line 726 by contrast intersects five pixels and runs approximately horizontally, i.e. parallel to the rows of the pixel field 720. It is clear from this illustration that the course of an individual hair 710 through the pixel field can have an influence on the measurement accuracy. This can also be referred to as quantization accuracy and is based on the fact that a pixel in a binary image can assume only precisely one state. On account of these effects, for the determination of the hair thickness it can be advisable to use length portions of an individual hair that run substantially vertically or horizontally in the pixel field 720 or that do not exceed a predefinable value of an angle between the middle axis 712 and a row or a column of the pixel field 720, for example 10° to 15°. Here, the extent transverse to the middle axis 712 or longitudinal direction of a hair is understood to be this thickness of a hair.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

LIST OF REFERENCE SIGNS 10 device for determining hair thickness
90 housing
100 computing unit
102 processor
104 local memory
106 image data input interface
107 user interface
108 data transmission interface
109 data connection
110 user surface, input and output unit
119 data connection
120 image-capturing unit
123 holding element
125 reference face
130 external computing unit
135 transmission path
140 network
200 greyscale image
205 individual hair
210 scale
215 reference element
220 binary image
400 bar chart
500 computer program product
600 method
610-650 method steps
700 image
710 hair
712 middle axis
714, 726 diameter 720 pixel field
725 pixel

The invention claimed is:

1. A device for determining the thickness of hair, the device comprising:
a computing unit with a processor and a local memory, wherein the processor is connected to the local memory and configured to read data from the local memory and/or to write data into the local memory;
a user input/output unit configured for interaction with a user;
wherein the computing unit comprises:
an image data input interface for receiving image data of a hair ensemble including at least one individual hair, wherein the image data input interface is connected to the processor;
a user interface connected to the user input/output unit and to the processor;
wherein the computing unit is configured to process the image data of the at least one individual hair to compute a plurality of hair thickness values of the at least one individual hair, to generate a bar chart of the plurality of hair thickness values, and to output the bar chart to the user interface, wherein the computing unit is configured to process the hair ensemble to identify one or more hairs that are running at an incline, and exclude the identified one or more hairs that are running at an incline from the determining the plurality of hair thickness values,
wherein the bar chart includes a first axis that represents hair thickness and a second axis that represents a frequency of the hair thickness.

2. The device according to claim 1, wherein the computing unit is configured to receive a greyscale image via the image data input interface and to convert the greyscale image into a binary image before creating the plurality of hair thickness values.

3. The device according to claim 1, wherein the computing unit is configured to specify the plurality of hair thickness values in the bar chart in pixels.

4. The device according to claim 3, wherein the computing unit is configured to determine a scale of the at least one individual hair in a predefinable length unit and to convert the plurality of hair thickness values into the predefinable length unit and to display the plurality of hair thickness values in the predefinable length unit in the bar chart.

5. The device according to claim 3,
wherein the computing unit is configured to output the image data of the at least one individual hair on the user input/output unit;
wherein the user input/output unit is configured to receive an input which denotes a region of the at least one individual hair and to transmit the input to the computing unit;
wherein the computing unit is configured to limit the bar chart to a subset of the plurality of hair thickness values occurring in the at least one individual hair to the region denoted in the input.

6. The device according to claim 1,
wherein the computing unit is configured to determine treatment agents and/or use instructions for treatment agents for the hair on the basis of the bar chart of hair thickness and to output these agents and/or instructions to the user input/output unit.

7. The device according to claim 1, wherein the computing unit and the user interface are arranged in a common housing.

8. The device according to a claim 1,
wherein the computing unit comprises a data transmission interface;
wherein the data transmission interface is configured to exchange data with an external computing unit via a transmission path.

9. The device according to claim 1, further comprising:
an image-capturing unit configured to create a captured image of the hair ensemble that includes the at least one individual hair;
wherein the image-capturing unit is coupled to the image data input interface in order to transmit the captured image of the hair ensemble to the processor.

10. The device according to claim 9, further comprising a reference face;
wherein the reference face is coupled via a holding element to the image-capturing unit; and
wherein the reference face is configured for placement of the hair ensemble.

11. A method for determining the thickness of hair using a computing unit, the method comprising the following steps:
reading out a captured image of a hair ensemble;
supplying the captured image to the computing unit;
converting the captured image into a binary image;
processing the hair ensemble to identify one or more hairs that are running at an incline, and selecting at least one individual hair by excluding the identified one or more hairs that are running at an incline,
determining a plurality of hair thickness values from the at least one individual hair of the hair ensemble in the binary image;
creating a bar chart regarding the plurality of hair thickness values; and
outputting the bar chart to a user interface,
wherein the bar chart includes a first axis that represents hair thickness and a second axis that represents a frequency of the hair thickness.

12. The method according to claim 11, further comprising:
transmitting the captured image to an external computing unit;
wherein the steps of converting the captured image into a binary image and of determining the plurality of hair thickness values are performed at least partially by the external computing unit and the results of these steps are transmitted back to the computing unit.

13. The method according to claim 11, further comprising:
determining a treatment agent and/or use instructions for treatment agents on the basis of the bar chart regarding the plurality of hair thickness values; and
outputting the treatment agent and/or the use instructions to the user interface.

14. The method according to claim 11, wherein the plurality of hair thickness values in the binary image are determined in pixels and/or in a predefinable length unit.

15. The device of claim 1, wherein the computing unit is configured to process the hair ensemble to identify a plurality of individual hairs, wherein the computing unit is further configured to determine the plurality of hair thickness values from the plurality of individual hairs, wherein the computing unit is further configured to generate the bar chart from the plurality of hair thickness values from the plurality of individual hairs.

16. The device of claim 15, wherein the computing unit is configured to generate the bar chart from the plurality of hair thickness values from the plurality of individual hairs determined from a plurality of image data.

17. A device for determining the thickness of hair, the device comprising:
- a computing unit with a processor and a local memory, wherein the processor is connected to the local memory and configured to read data from the local memory and/or to write data into the local memory;
- a user input/output unit configured for interaction with a user;
- wherein the computing unit comprises:
- an image data input interface for receiving image data at least one individual hair, wherein the image data input interface is connected to the processor;
- a user interface connected to the user input/output unit and to the processor;
- wherein the computing unit is configured to process the image data of the at least one individual hair to compute a plurality of hair thickness values of the at least one individual hair, to generate a bar chart of the plurality of hair thickness values, and to output the bar chart to the user interface,
- wherein the bar chart includes a first axis that represents hair thickness and a second axis that represents a frequency of the hair thickness,
- wherein the computing unit is further configured to determine whether the image data is optically distorted and when the image data is determined to be optically distorted, to compensate for the distortion when determining the plurality of hair thickness values, and
- wherein the computing unit is further configured to identify a first reference element that runs horizontally, identify a second reference element that runs vertically, and determine whether the image data is optically distorted in a vertical direction based on the first reference element, and determine whether the image data is optically distorted in a horizontal direction based on the second reference element.

* * * * *